United States Patent [19]

Bloom

[11] 4,034,745
[45] July 12, 1977

[54] CARDIOTACHOMETER

[76] Inventor: Kenneth A. Bloom, Wellington Arms Apt., Apt. 6E, Lenox, Mass. 01240

[21] Appl. No.: 666,676

[22] Filed: Mar. 15, 1976

[51] Int. Cl.² .......................................... A61B 5/04
[52] U.S. Cl. ......................... 128/2.06 F; 324/78 D
[58] Field of Search ................ 128/2.05 P, 2.05 R, 128/2.05 T, 2.06 E, 2.06 F, 2.06 R; 328/130; 324/186, 78 D; 307/325 R

[56] References Cited

U.S. PATENT DOCUMENTS

| 3,384,075 | 5/1968 | Mitchell | 128/2.06 F |
| 3,599,628 | 8/1971 | Abbenante et al. | 128/2.06 F |
| 3,717,140 | 2/1973 | Greenwood | 128/2.06 F |
| 3,829,785 | 8/1974 | Schroder et al. | 328/130 |
| 3,837,333 | 9/1974 | Bruckheim | 128/2.06 F |
| 3,858,574 | 1/1975 | Page | 128/2.05 T |
| 3,909,714 | 9/1975 | Nakano | 324/78 D |
| 3,921,624 | 11/1975 | Vogelman | 128/2.06 F |
| 3,928,798 | 12/1975 | Valis | 307/225 R |

Primary Examiner—William E. Kamm
Attorney, Agent, or Firm—McAulay, Fields, Fisher & Goldstein

[57] ABSTRACT

The heart beat pulses of an ECG signal are counted by a digital counter. A timing signal loads the count into a register once each 15 seconds and resets the counter to zero. Four intermediate registers hold four successive counts. The output of the four registers is summed and applied through a multiplexer to an eight bit main register. When the equipment is first turned on, the multiplexer is forced into a special state in which it loads the output of the counter into the upper six bits of the eight bit main register thereby providing a main register output that is four times the value in the counter. The main register output is displayed providing a digital heart beat reading in pulses per minute. Once each 15 seconds during the first minute of operation, this main register is updated from the counter to provide a new output reading. At the end of the first minute, the state of the multiplexer is switched and from there on in, the sum output of the four intermediate registers is applied to the main register to provide a heart beat rate based on a full one minute count. This count is also updated once each 15 seconds because the four intermediate registers are in tandem.

15 Claims, 2 Drawing Figures

CARDIOTACHOMETER

BACKGROUND OF THE INVENTION

When a cardiotachometer is used in a hospital for the monitoring of critically ill patients in intensive care units, it is important that information be proided as soon as possible after connecting the cardiotachometer to the patient and it is further important that the information provided be as accurate as possible. In calculating a heart beat rate, it is preferable to count heart beats for at least one full minute to minimize the effect of error due to occasional noise in the electrical system or spurious heart beat signals. Calculating a rate in beats per minute based on a count during fractions of a second multiplies any error in the count. Yet, 1 minute is frequently too long to wait for a doctor to get the first information from the cardiotachometer.

Accordingly, it is a major purpose of this invention to provide a cardiotachometer which is versatile in that it meets both of these objectives in that it provides a reading as quickly as possible while then providing a more accurate reading after a minute has passed.

Because these caridotachometers are used for relatively long term monitoring purposes, it is also a purpose of this invention to provide a cardiotachometer which will provide regular, continuous and automatic updating of the heart beat rate. It is important that this updating occur more frequently than once a minute so that any sudden change in the patient's heart beat will be noticed and an appropriate warning signal can be actuated.

At the same time, it is important that the updating be in accordance with a routine which will minimize the effect on the output heart beat rate of a noise spike.

In any monitoring operation, it is important that the measurement data provided be relatively unambiguous and that its significance not be subject to misinterpretation or misunderstanding. Accordingly, it is an important purpose of this invention to provide an unambiguous readout in a device which also provides the dual function of a relatively speedy readout as well as an ultimately accurate readout.

In order to provide the benefits of versatility and unambiguous presentation in a context that will be used as widely as possible, it is a further purpose of this invention to meet these objectives in a device that is relatively simple, reliable, easy to maintain and inexpensive.

Patents illustrating known cardiotachometer techniques are U.S. Pat. Nos. 3,202,149, 3,603,769, 3,773,038 and 3,807,388.

BRIEF DESCRIPTION OF THE INVENTION

In brief, this invention employs an ECG pulse counter and a clock that provides a timing pulse once for each 15 seconds. The timing pulse is used to transfer the reading out of the ECG counter once every 15 seconds into a register. A timing generator responds to each timing pulse to provide a reset pulse to reset the counter after its contents have been transferred. During the first minute of operation after the cardiotachometer has been turned on, the output of the ECG counter is transferred, once each 15 seconds, to the upper six bits of an eight bit output register thereby providing an output which has four times the value of the ECG counter. In this fashion, the output register provides a number representing the heart beat rate in pulses per minute.

The eight bit output from the register is applied to a BCD converter, the output of which in turn is applied to a seven segment driver so that a visual numerical display of the heart beat rate in pulses per minute will be available to the doctor or other attendant.

At the same time, the timing generator responds to each timing pulse by generating a series of loading pulses. One loading pulse causes a transfer of data from the ECG counter to the first of four intermediate registers connected in tandem. Other loading pulses cause the following to occur in sequence once each 15 seconds. The reading in the fourth intermediate register is cancelled. The reading in the third intermediate register is then transferred to the fourth intermediate register. The reading in the second intermediate register is then transferred to the third intermediate register. The reading in the first intermediate register is then transferred to the second intermediate register. And finally the reading in the ECG counter is transferred to the first intermediate register. Thus after the first minute, the four intermediate registers each hold a value equal to the number of ECG pulses in successive b 15 second intervals. The outputs of the four intermediate registers are added together in an adder.

After the first four successive timing pulses, and thus after 1 minute has passed, the ECG counter is decoupled from the eight bit output register and the output of the adder is then coupled to the output register. From this point on, the display will read the accurate heart beat in pulses per minute over the full previous minute and further will be updated once each 15 seconds.

DESCRIPTION OF THE PREFERRED EMBODIMENTS

Figure 1:
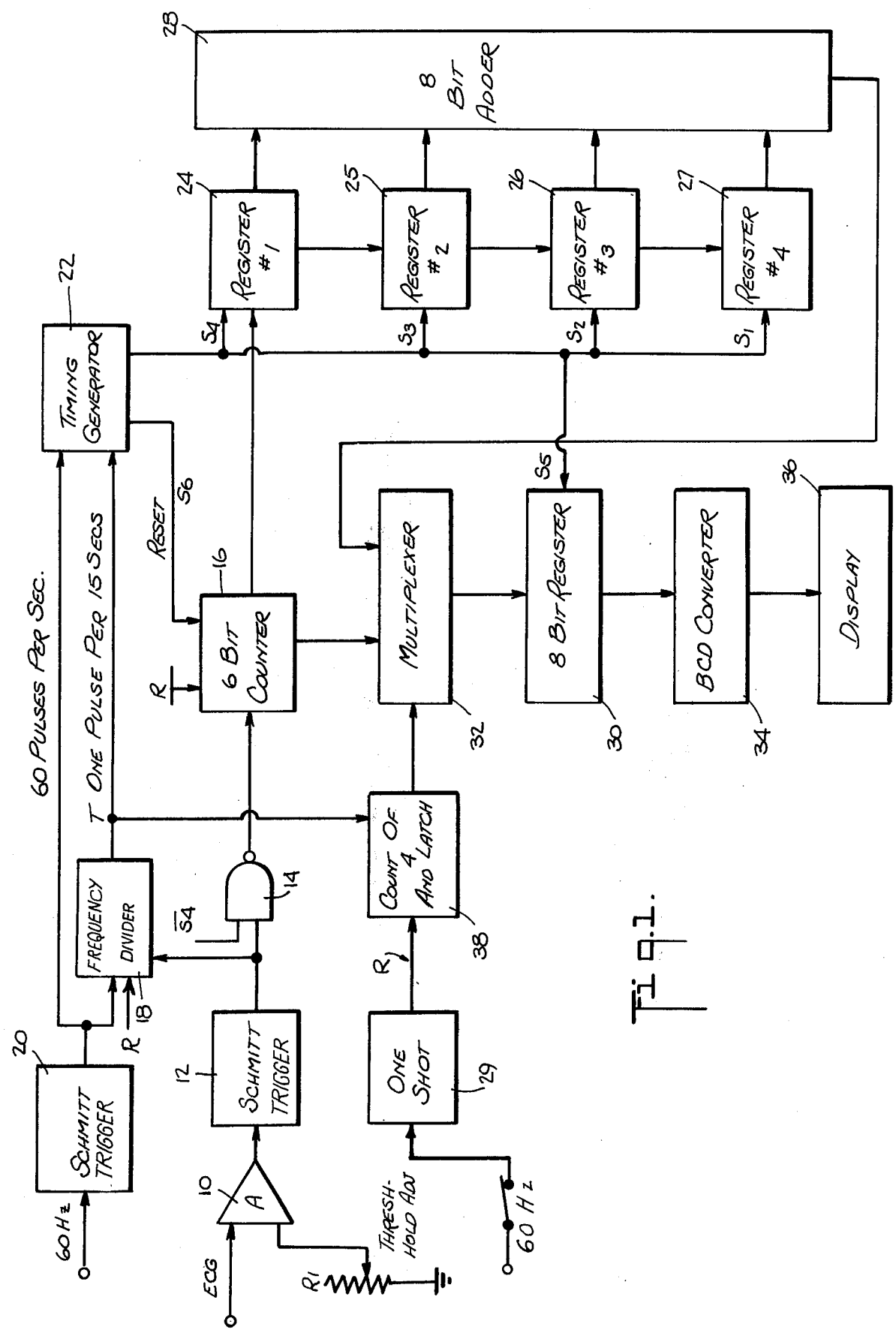
FIG. 1 is a block diagram illustrating the device of this invention.

With reference to FIG. 1, an ECG signal is supplied to the input of an amplifier 10. The amplifier 10 is biased by an adjustable resistor R1 to provide a threshold for screening out all of the ECG components which do not reflect the major component representing the heart beat rate. In particular only ECG pulses which exceed the predetermined threshold value will pass through the amplifier 10 to the Schmitt trigger 12. The Schmitt trigger 12 is used for the usual pulse shaping purpose to provide a pulse having a predetermined width and height for each heart beat pulse. The output of the Schmitt trigger 12 is applied, through a gate 14, to a counter circuit 16 having six bit capacity.

When the ECG signal is first supplied to the equipment, the first pulse out of the Schmitt trigger 12 turns on a digital frequency divider. The frequency divider 18 is composed of standard digital countdown circuitry and operates off a 60 pulse per second (pps) pulse train from the Schmitt trigger 20 that in turn is responsive to the standard 60 Hertz line frequency. This 60 pps pulse train is applied as an input to a timing generator 22 and, for purposes described in greater detail further on, is used as the basis for a series of sequencing signals S1 through S6. The frequency divider 18, once turned on, provides an output T which is a pulse once each 15 seconds. This pulse is applied to the timing generator 22 and is the basic timing pulse in the equipment. The timing generator 22 responds to the basic timing pulse T to generate, in response thereto, a series of six successive sequencing pulses S1 through S6. The function of these sequencing pulses S1–S6 is to assure that the counter 16 output is read once each 15 seconds and is stored in the appropriate sequence in the four registers 24, 25, 26 and 27.

More specifically what occurs is that when power is turned on, a one shot pulse generator 29 provides a power-on reset pulse R, which is applied to the counter 16 and the frequency divider 18 to set the counter 16 and the frequency divider 18 at zero. The Schmitt trigger 12 output pulses representing heart beats are counted by the counter 16. At the end of 15 seconds the counter 16 value is read by the first register 24. The sequencing pulse S4, which is one of the pulses generated at the end of each 15 second time period, enables the register 24 and loads the value of the counter 16 into the register 24. A reset pulse S6 which is generated after the enabling pulse S4 sets the counter 16 back to zero. The counter 16 then proceeds to count pulses for the next 15 second time period.

At the end of the next 15 second interval, the sequencing pulse S3 enables the second register 25 and thus loads it with the value in the first register 24. The sequencing pulse S4 then loads the first register 24 with the new value in the counter 16. The reset pulse S6 starts the counter 16 back at zero and the procedure repeats at the end of the next 15 second time period at which time the sequencing pulse S2 loads the third register 26 with the value in the second register 25. An analogous sequence occurs at the end of the fourth 15 second time period in which the sequencing signal S1 loads the fourth register 27 with the value held in the third register 26. Thus at the end of four 15 second time periods, the registers 24, 25, 26 and 27 each hold a value from the counter 16 representative of successive 15 second heart beat counts. An adder 28 having eight bits provides an output which is the sum of the values in the four registers 24–27. Thus after the first 60 seconds the adder 28 provides an accurate count of the number of heart beats in the proceeding 60 seconds. Because of the read-out from the counter 16 once each 15 seconds, the value provided by the adder 28 is up-dated once each 15 seconds. For this to occur properly the sequencing signals must have the sequence indicated by their reference numbers; specifically, the sequence signal S1 must come first, S2 after S1, S3 after S2, S4 after S3 and S5 (its function is described below) after S4. This sequencing is important so that the registers 24–27 can operate in the proper sequence. The fifth sequencing signal S5 enables the register 30, which has an eight bit capacity, thus causing the output of the adder 28 to be loaded into this register 30 through a multiplexer unit 32.

The purpose of this multiplexer unit 32 is to provide a meaningful value for the register 30 output during the first 60 seconds after the equipment is turned on. During the normal running of the equipment after the first 60 seconds, the multiplexer 32 simply provides a pass through of the value in the adder 28 to the register 30. The output from the register 30 is processed by a binary to BCD converter 34 so as to energize a seven segment display and thus provide a digital readout for the doctor or attendant.

During the first minute that the equipment has been turned on, it is desirable to have as accurate a reading as possible for the doctor. Obviously, the full accuracy of a 1 minute count cannot be obtained until 1 minute has passed. But, a preliminary readout can be provided which can aid in immediate diagnosis and provide some time saving for the personnel involved.

This function is provided through the multiplexer 32 which has parallel inputs from the counter 16 and from the adder 28 but which provides only one of these two values as an output. Which value is provided as the multiplexer 32 output is a function of a state signal from the unit labeled "Count-Of 4 and Latch" 38. The unit 38 is essentially a counter which is set to zero by the reset signal R when power is turned on and which then counts the basic timing pulses T put out by the clock 18 until a count of four is reached. Prior to the count of four, the output of the counter 38 has one state (high or low) and upon the count of four the state of the counter 38 switches. Thus prior to 1 minute, the state signal input to the multiplexer 32 has one value and after 60 seconds, the state signal input to the multiplexer 32 has the other value. The value of the state signal determines the state of the multiplexer 32. Prior to the count of four, the state signal places the multiplexer 32 in a state whereby the output of the counter 16 is loaded into the register 30 once each 15 seconds. The sequencing pulse S5 enables the register 30 and causes it, once each 15 seconds, to read the output from the multiplexer 32. Since the output from the multiplexer 32 is the counter 16 output prior to the first minute having elapsed, the register 30 will read the counter 16 output. However, in this initial state situation, the output from the multiplexer 32 is applied to the upper six bits of the eight bit register 30 thereby automatically multiplying the value held by the register 30 by four. In this fashion the counter 16 reading at the end of the first 15 seconds is connected through the multiplexer 32 to the upper six bits of the registers 30 so that the value shown at the display 36 is four times that of the counter 16 and thus is a rate representing heart beats per minute. Thus at the end of 15 seconds after the equipment has been turned on, a heart beat rate in pulses per minute is provided at the display. This value does not have the full accuracy available after one minute of time has passed but it is as accurate a rate as can provided in 15 seconds and does provide a value without requiring the observer to wait the full minute.

The counter 16 counts on a rising edge of a pulse. In the embodiments shown, a Nand gate 1 is preferably used between the Schmitt trigger 12 and counter 16 so as to provide a means for preventing the counter 16 from receiving an input pulse during the time when the counter 16 value is being loaded into the first register 24. This loading operation occurs during the 1/60th of a second duration of the sequencing signal S4. During this period the $\overline{S4}$ signal applied as one of the inputs to the Nand gate 14 prevents any pulses from getting through the Nand gate 14 to the counter 16. More particularly, the $\overline{S4}$ input to the Nand gate 14 is normally high and thus the output from the Nand gate 14 is normally high. When a pulse comes through the Schmitt trigger 12, the output of the Nand gate 14 drops low. The termination of the pulse causes the output of the Nand gate to go high and thus the counter 16 reads one count. However, when the sequencing pulse S4 is generated, $\overline{S4}$ drops low, which does not change the output of the Nand gate 14 from its normally high state. But when a pulse comes through the Schmitt circuit 12, it will have no effect on the normally high output of the Nand gate 14.

Figure 2:
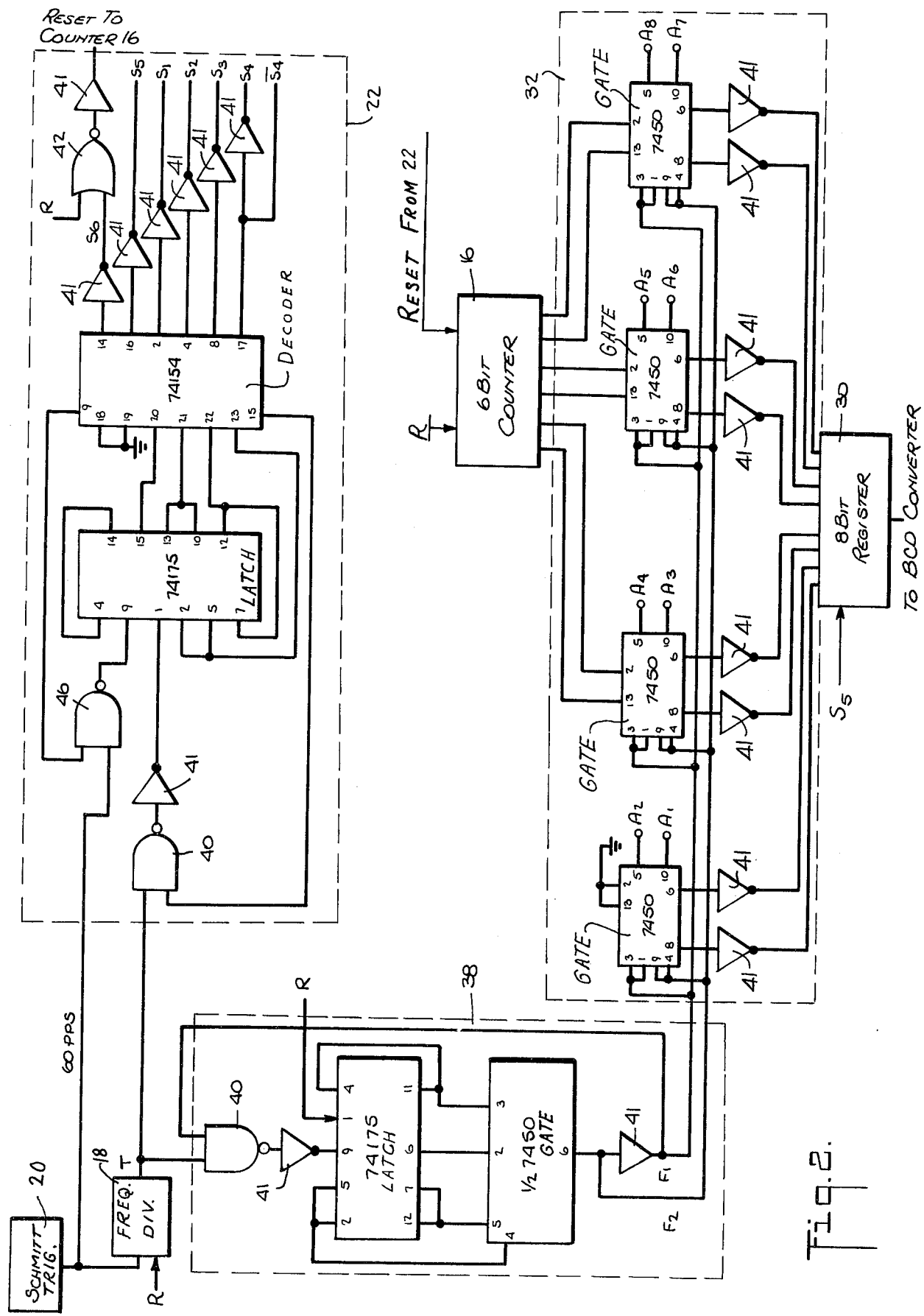
FIG. 2 is a more schematic illustration of certain portions of the FIG. 1 diagram to illustrate the relationship between certain integrated circuits employed to constitute the timing generator, multiplexer and count of four/latching unit.

FIG. 2 shows the circuit arrangements employing various integrated circuits (I.C.) that constitute the timing generator 22, the multiplexer 32 and the count of four latching circuit 38. As shown therein, various Nand gates 40, inverters 41 and a Nor gate 42 are employed together with the integrated circuits as shown to provide these units. The integrated circuits are designated by number and are known units having the terminal designations indicated in FIG. 2. It is not believed that further written description, apart from FIG. 2, is required to describe the design or operation of these three units in this embodiment of the invention.

In the timing generator 22, the IC 74154 is commonly known as a decoder and the IC 74175 is used to latch an address to the decoder 74154. The basic timing signal T, which is a pulse once each 15 seconds, is fed to the timing generator through a Nand gate 40 while the 60 p.p.s. signal is fed from the Schmitt trigger 20 to the timing generator through another Nand gate 46. In effect the timing generator operates as a complicated gate which is opened in response to each basic timing signal T to let through six successive pulses from the 60 p.p.s. pulse train. The six successive pulses, in succession, are the sequencing pulses S1, S2, S3, S4, S5 and S6. The output $\overline{S4}$ is simply the inverse of S4 and is a high signal from pin 17 of the decoder 74154 except for the 1/60th of a second when that terminal goes low to generate the S4 pulse through the associate inverter 41.

In the embodiment that has been built, the Nor gate 42 together with the associated inverter 41 provides an Or function so that the S6 pulse and the power-on reset pulse R can be applied on the same line to reset the counter 16. The power-on reset pulse R is generated by a one-shot 29 which in one embodiment is provided by an appropriately wired intermediate circuit 74121 (not shown in FIG. 2).

For convenience in comprehension, in FIG. 1, the S6 reset signal and the power-on reset signal R are shown as inputs on two separate lines to the counter 16. In the embodiment actually built, it was more convenient to provide the arrangement shown in FIG. 2.

The multiplexer 32 is composed substantially of four IC 7450 units, which perform a gating function. The eight outputs from the eight bit adder 28 are provided as the inputs A1 through A8 to these IC units. The six bit output from the six bit counter 16 is provided as the six inputs shown in FIG. 2 to three of the IC 7450 units. It is because of this input connection to the multiplexer 32 that the counter 16 output value is automatically multiplied by four when it is passed through the multiplexer 32 to the register 30. The state signals F1, F2 to the 7450 circuits determine which set of inputs will be passed through to the eight bit register 30 and stored there each time the register 30 is enabled by a sequencing pulse S5.

The count of four and latching circuit 38 is reset when power is turned on by a power-on reset signal R and then proceeds to count the timing pulses T. When reset, the output F1 is high. This output F1 is applied to the Nand gate 40 so that input pulses T will provide corresponding pulse inputs to the IC 74175. Once a count of four has been completed, the output signal F1 will drop low thereby preventing any further pulses from passing through the Nand gate 40 and thus latching the unit 38 at a count of four. The corresponding switching in the state of the output signals F1 and F2 results in a corresponding switch of the state of the 7450 integrated circuits in the multiplexer 32 to provide a switch in the output of the multiplexer from a value provided by the counter 16 to a value provided by the adder 28.

What is claimed is:
1. A cardiotachometer comprising:
   a sensor responsive to an ECG signal to provide a pulse train representing heart beats,
   a clock providing a timing signal once each n seconds,
   counting means responsive to said pulse train and to said timing signal to provide a count of the number of said pulses in said pulse train each n second time period, there being m of said time periods in sixty seconds, 'intermediate storage means coupled to the output of said counter means and to said timing signal to provide a count of the number of pulses in said pulse train during m successive n second time periods,
   updating means coupled to said timing signal and to said intermediate storage means to update the count held by said intermediate storage once each n seconds,
   a p bit output storage means,
   multiplexer means having a first and second state, said multiplexer means when in said first state interfacing between said counter and the upper bits of said output storage means, said multiplexer means when in said second state interfacing between said intermediate storage means and said output storage means, and
   latching means having a first state output signal and a second state output signal, said first state output signal of said latching means forcing said multiplexer into its first state and said second state output signal from said latching means forcing said multiplexer into its second state, said latching means being responsive to said timing signals to be switched into its second state in response to the mth one of said timing signals after said clock is initially turned on,
   said timing signal being coupled to said output storage means to update said output storage means once each n seconds.
2. The cardiotachometer of claim 1, wherein:
   said n second time period is 15 seconds, and said multiplexer when in said first state interfacing between said counter and the upper p-2 bits of said output storage means.
3. The cardiotachometer of claim 2 wherein:
   said intermediate storage means and said output storage means are registers.
4. The cardiotachometer of claim 3 wherein:
   said clock is responsive to a first heart beat signal from said ECG signal to be turned on by said first heart beat signal.
5. The cardiotachometer of claim 4 further comprising:
   means responsive to the turning on of the cardiotachometer to provide a turn-on signal, said counting means and said clock being reset to zero by said turn-on signal and said latching means being switched into said first state by said turn-on signal.

6. The cardiotachometer of claim 3 further comprising:
means responsive to the turning on of the cardiotachometer to provide a turn-on signal, said counting means being reset by said turn-on signal and said latching means being switched into said first state by said turn-on signal.

7. The cardiotachometer of claim 2 wherein:
said clock is responsive to a first heart beat signal from said ECG signal to be turned on by said first heart beat signal.

8. The cardiotachometer of claim 2 further comprising:
means responsive to the turning on of the cardiotachometer to provide a turn-on signal, said counting means being reset by said turn-on signal and said latching means being switched into said first state by said turn-on signal.

9. The cardiotachometer of claim 1 wherein:
said intermediate storage means and said output storage means are registers.

10. The cardiotachometer of claim 1 wherein:
said clock is responsive to a first heart beat signal from said ECG signal to be turned on by said first heart beat signal.

11. The cardiotachometer of claim 1 further comprising:
means responsive to the turning on of the cardiotachometer to provide a turn-on signal, said counting means being reset by said turn-on signal and said latching means being switched into said first state by said turn-on signal.

12. A cardiotachometer comprising:
sensing means responsive to an ECG signal to provide a pulse train representing heart beats,
a six bit counter responsive to said pulse train to provide a count of the number of pulses in said train,
a clock providing a timing pulse once each 15 seconds,
first, second, third and fourth intermediate registers connected in tandem, the output of said counter being connected to the input of said intermediate register, the output of said first intermediate register being coupled to the input of said second intermediate register, the output of said second intermediate register being coupled to the input of said third intermediate register and the output of said third intermediate register being coupled to the input of said fourth intermediate register,
an adder connected to the output of said four intermediate registers to provide a sum output value equal to the sum of the values held in said four intermediate registers,
timing generator means responsive to each of said timing pulses to provide a set of six successive sequencing pulses, the first four of said sequencing pulses being coupled respectively to said fourth, third, second and first intermediate registers, to sequentially load the content of said third intermediate register into said fourth intermediate register, load the content of said second intermediate register into said third intermediate register, load the content of said first intermediate register into said second intermediate register and load the content of said counter into said first intermediate register,
an eight bit output register,
multiplexer means between the output of said counter and said output register, said multiplexer means also being between the output of said adder and said output register,
said multiplexer having a first state in which the output of said counter is applied to the upper six bits of said output register and a second state in which the output of said adder is applied to said output register,
latching means responsive to said timing pulses to force said multiplexer into said first state upon generation of the first of said timing pulses after turn-on of said clock and to force said multiplexer into said second state upon generation of the fourth of said timing pulses after turn-on of said clock,
the fifth of said sequencing pulses coupled to said output register to load said output register once every 15 seconds,
the sixth of said sequencing pulses coupled to said counter to reset said counter once every 15 seconds, and
display means responsive to said output register to provide a visual reading representing the value stored in said output register.

13. The cardiotachometer of claim 12 wherein:
said clock is responsive to a first heart beat signal from said ECG signal to be turned on by said first heart beat signal.

14. The cardiotachometer of claim 13 further comprising:
means responsive to the turning on of the cardiotachometer to provide a turn-on signal, said counter and said clock means being reset to zero by said turn-on signal and said latching means being switched into said first state by said turn-on signal.

15. The cardiotachometer of claim 12 further comprising:
means responsive to the turning on of the cardiotachometer to provide a turn-on signal, said counter being reset by said turn-on signal and said latching means being switched into said first state by said turn-on signal.

* * * * *